United States Patent
Kim et al.

(10) Patent No.: US 10,694,997 B2
(45) Date of Patent: Jun. 30, 2020

(54) APPARATUS FOR DETECTING BIOMETRIC INFORMATION OF LIVING BODY

(71) Applicant: SAMSUNG ELECTRONICS CO., LTD., Suwon-si (KR)

(72) Inventors: Younho Kim, Hwaseong-si (KR); Yongjoo Kwon, Yongin-si (KR); Jaemin Kang, Seoul (KR); Sunkwon Kim, Suwon-si (KR); Sangyun Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/001,753

(22) Filed: Jan. 20, 2016

(65) Prior Publication Data

US 2016/0206221 A1 Jul. 21, 2016

(30) Foreign Application Priority Data

Jan. 21, 2015 (KR) ........................ 10-2015-0010025

(51) Int. Cl.
*A61B 5/024* (2006.01)
*A61B 5/00* (2006.01)
*A61B 5/021* (2006.01)

(52) U.S. Cl.
CPC .......... *A61B 5/681* (2013.01); *A61B 5/02433* (2013.01); *A61B 5/02125* (2013.01);
(Continued)

(58) Field of Classification Search
None
See application file for complete search history.

(56) References Cited

U.S. PATENT DOCUMENTS 5,255,686 A 10/1993 Takeda et al.
6,475,153 B1 11/2002 Khair et al.
(Continued)

FOREIGN PATENT DOCUMENTS

CN 101828908 A 9/2010
CN 102088899 A 6/2011
(Continued)

OTHER PUBLICATIONS

Communication dated May 23, 2016 issued by European Patent Office in counterpart European Application No. 16151653.9.
(Continued)

*Primary Examiner* — Erica S Lee
(74) *Attorney, Agent, or Firm* — Sughrue Mion, PLLC

(57) ABSTRACT

An apparatus for detecting biometric information of a living body detects a pulse wave and extracts the biometric information of the living body in a non-invasive method. The apparatus for detecting biometric information includes a surface pulse wave measurement unit for measuring a surface pulse wave of an object. The surface pulse wave measurement unit includes at least one light source that radiates incoherent light and at least one photodetector that measures an intensity of light radiated by the at least one light source and reflected from a surface of the object. The surface pulse wave measurement unit measures the surface pulse wave of the object based on a change in the intensity of the light reflected from the surface of the object.

16 Claims, 12 Drawing Sheets

(52) U.S. Cl.
CPC ... *A61B 5/02438* (2013.01); *A61B 2562/0233* (2013.01); *A61B 2562/04* (2013.01)

(56) References Cited

U.S. PATENT DOCUMENTS

| | | | |
|---|---|---|---|
| 7,544,168 | B2 | 6/2009 | Nitzan |
| 2002/0188210 | A1 | 12/2002 | Aizawa |
| 2011/0009712 | A1 | 1/2011 | Fayram et al. |
| 2011/0054277 | A1* | 3/2011 | Pinter ............... A61B 5/0205 600/310 |
| 2011/0118564 | A1 | 5/2011 | Sankai |
| 2012/0116235 | A1* | 5/2012 | Trumble ............ A61B 5/7415 600/485 |
| 2012/0176599 | A1* | 7/2012 | Leung ................ G01N 21/31 356/39 |
| 2014/0051941 | A1 | 2/2014 | Messerschmidt |
| 2014/0243689 | A1 | 8/2014 | Yamashita et al. |
| 2014/0275854 | A1* | 9/2014 | Venkatraman ...... A61B 5/721 600/301 |
| 2015/0057511 | A1* | 2/2015 | Basu ............... A61B 5/02433 600/323 |
| 2015/0135310 | A1* | 5/2015 | Lee .................. A61B 5/681 726/20 |
| 2015/0141774 | A1 | 5/2015 | Ogawa et al. |
| 2015/0190062 | A1* | 7/2015 | Han .................. A61B 5/7221 600/479 |
| 2017/0049340 | A1* | 2/2017 | Cho .................. A61B 5/0285 |

FOREIGN PATENT DOCUMENTS

| | | |
|---|---|---|
| CN | 102106725 A | 6/2011 |
| CN | 102334986 A | 2/2012 |
| CN | 103027690 A | 4/2013 |
| KR | 10-0820159 B1 | 4/2008 |
| KR | 10-0849667 B1 | 8/2008 |
| KR | 10-0944710 B1 | 2/2010 |
| WO | 2014/021335 A1 | 2/2014 |

OTHER PUBLICATIONS

Communication dated Jan. 18, 2018, issued by the European Patent Office in counterpart European Application No. 16 151 653.9.
Communication dated Oct. 9, 2019 issued by the State Intellectual Property Office of P.R. China in counterpart Chinese Application No. 201610040843.3.

* cited by examiner

APPARATUS FOR DETECTING BIOMETRIC INFORMATION OF LIVING BODY

CROSS-REFERENCE TO RELATED APPLICATION

This application claims priority from Korean Patent Application No. 10-2015-0010025, filed on Jan. 21, 2015 in the Korean Intellectual Property Office, the disclosure of which is incorporated herein by reference in its entirety.

BACKGROUND

1. Field

Apparatuses and methods consistent with exemplary embodiments relate to detecting biometric information of living body, and more particularly, to detecting a pulse wave and extracting the biometric information of the living body in a non-invasive manner.

2. Description of the Related Art

A method of detecting biometric information, such as, a pulse wave, may be divided into an invasive method and a non-invasive method. Recently, the non-invasive method has been increasingly used because a pulse wave may be detected in a simple manner without causing pain to an examinee.

SUMMARY

According to an aspect of an exemplary embodiment, there is provided an apparatus for detecting biometric information including a surface pulse wave measurement unit configured to measure a surface pulse wave of an object, and a biometric signal extractor configured to extract a plurality of biometric signal parameters based on the measured surface pulse wave of the object, wherein the surface pulse wave measurement unit includes at least one light source configured to radiate incoherent light, at least one photodetector configured to measure an intensity of light radiated by the at least one light source and reflected from a surface of the object, and a guide portion configured to fix the at least one light source and the at least one photodetector to be separated from the surface of the object, and wherein the surface pulse wave measurement unit is further configured to measure a surface pulse wave of the object based a change in the intensity of the light reflected from the surface of the object.

One light source of the at least one light source and one photodetector of the at least one photodetector may be disposed adjacently to each other to form a pair.

The guide portion may include at least one partition disposed between the pair of the light source and the photodetector and another pair of another light source of the at least one light source and another photodetector of the at least one photodetector.

A plurality of photodetectors that includes the at least photodetector may be disposed around one light source.

The guide portion may include a plurality of partitions, each of the plurality of partitions being disposed between adjacent ones of the plurality of photodetectors.

The biometric signal extractor may include a peak detector configured to extract a peak of the measured surface pulse wave, a dicrotic notch detector configured to extract a dicrotic notch of the measured surface pulse wave, a heart rate detector configured to count a number of surface pulse wave signals per unit time, wherein the number of surface pulse waves includes the measured surface pulse wave, and a pulse time detector configured to extract a pulse transit time (PTT) of the measured surface pulse wave between at least two different positions on the object.

The apparatus may further include an analyzer configured to analyze biometric information including blood vessel elasticity, a flow rate velocity, a degree of arteriosclerosis, a systolic blood pressure, or diastolic blood pressure of a blood vessel, based on the plurality of parameters including the peak, the dicrotic notch, the heart rate, or the PTT.

According to an aspect of another exemplary embodiment, there is provided an apparatus for detecting biometric information including: a surface pulse wave measurement unit configured to measure a surface pulse wave of an object, a photo-plethysmogram measurement unit configured to measure a photo-plethysmogram (PPG) signal of the object, and a biometric signal extractor configured to extract a plurality of biometric signal parameters based on the measured surface pulse wave and the measured PPG signal, wherein the surface pulse wave measurement unit includes at least one light source, at least one photodetector configured to measure an intensity of light radiated by the at least one light source and reflected from a surface of the object, and a guide portion configured to fix the at least one light source and the at least one photodetector to be separated from the surface of the object The PPG measurement unit may include at least one light source disposed to be in contact with the surface of the object, and at least one photodetector disposed to be in contact with the surface of the object.

One light source of the at least one light source of the surface pulse wave measurement unit and one photodetector of the at least one photodetector of the surface pulse wave measurement unit may be disposed adjacently to each other form a pair. One light source of the at least one light source of the PPG measurement unit and one photodetector of the at least one photodetector of the PPG measurement unit are disposed next to each other form a pair.

The guide portion may include at least one partition disposed between the pair of the light source and the photodetector of the surface pulse wave measurement unit.

The pair of the surface pulse wave measurement unit and the pair of the PPG measurement unit may be disposed adjacently to each other, and the guide portion may include at least one partition between the pair of the surface pulse wave measurement unit and the pair of the PPG measurement unit.

The pair of the surface pulse wave measurement unit may be fixed to an upper portion of the partition and the pair of the PPG measurement unit may be fixed to a lower portion of the partition.

A plurality of photodetectors of the surface pulse wave measurement unit that includes the at least one photodetector may be disposed around the at least one light source of the surface pulse wave measurement unit.

The PPG measurement unit may include a plurality of photodetectors disposed to be in contact with the surface of the object. The plurality of photodetectors of the PPG measurement unit may be disposed around the at least one light source of the surface pulse wave measurement unit.

The plurality of photodetectors of the surface pulse wave measurement unit and the plurality of photodetectors of the PPG measurement unit may be alternately disposed.

The biometric signal extractor may include a direct current (DC) component detector configured to extract a DC component of the PPG signal, a peak detector configured to extract a peak of the PPG, a dicrotic notch detector configured to extract a dicrotic notch of the PPG signal, a heart rate detector configured to count a number of pulse wave signals per unit time, and a pulse time detector configured to extract a pulse transit time (PTT) of the PPG signal between at least two different positions on the object.

The apparatus may further include an analyzer configured to analyze biometric information including blood vessel elasticity, a flow rate velocity, a degree of arteriosclerosis, a systolic blood pressure, or a diastolic blood pressure of a blood vessel based on the plurality of parameters including the DC component, the peak, the dicrotic notch, the heart rate, or the PTT.

The apparatus may further include a display unit configured to display the extracted plurality of parameters or the analyzed biometric information.

The surface pulse wave measurement unit and the PPG measurement unit may be disposed in a wearing unit wearable by the object.

The light radiated by the at least one light source may be incoherent light, and the surface pulse wave measurement unit may be configured to measure the surface pulse wave of the object based on a change in the intensity of the light reflected from the surface of the object.

BRIEF DESCRIPTION OF THE DRAWINGS

The above and/or other aspects will be more apparent by describing certain embodiments, with reference to the accompanying drawings, in which.

DETAILED DESCRIPTION

Figure 1:
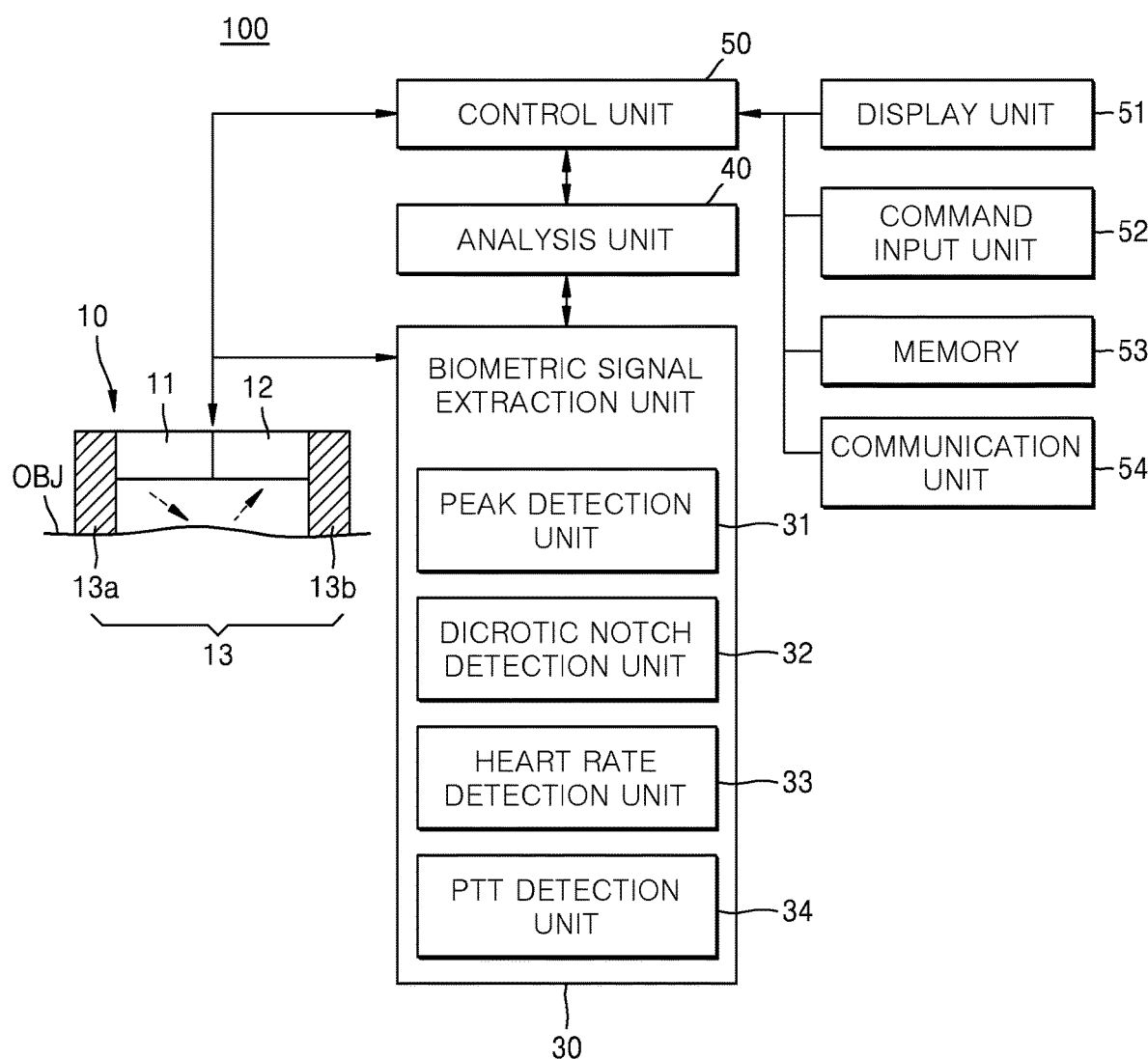
FIG. 1 is a block diagram schematically illustrating a structure of an apparatus for detecting biometric information according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

As used herein, the term "and/or" includes any and all combinations of one or more of the associated listed items. Expressions such as "at least one of," when preceding a list of elements, modify the entire list of elements and do not modify the individual elements of the list.

In the drawings, the thicknesses of layers and regions are exaggerated for clarity. It will also be understood that when a layer is referred to as being "on" another layer or substrate, it can be directly on the other layer or substrate, or intervening layers may also be present.

FIG. 1 is a block diagram schematically illustrating a structure of an apparatus for detecting biometric information according to an exemplary embodiment. FIG. 1 illustrates an apparatus 100 that may detect biometric information according to the present exemplary embodiment. The apparatus 100 may include a surface pulse wave measurement unit 10, a biometric signal extraction unit (e.g., biometric signal extractor) 30, an analysis unit (e.g., analyzer) 40, and a control unit (e.g., controller, processor, computing device, and the like) 50. While the surface pulse wave measurement unit 10 is disposed on a surface of an object OBJ, the surface pulse wave measurement unit 10 may optically measure a surface pulse wave of the object OBJ and the biometric signal extraction unit 30 may extract a plurality of biometric signal parameters based on a surface pulse wave of the object OBJ measured by the surface pulse wave measurement unit 10. The analysis unit 40 may analyze biometric information based on various biometric signal parameters extracted by the biometric signal extraction unit 30. The control unit 50 may control the operations of the surface pulse wave measurement unit 10, the biometric signal extraction unit 30, and the analysis unit 40.

According to the present embodiment, the surface pulse wave measurement unit 10 may include a light source 11 that radiates incoherent light, a photodetector 12 that may measure intensity of light radiated by the light source 11 and reflected from a surface of the object OBJ, and a guide portion 13 that may fix the light source 11 and the photodetector 12 so that the light source 11 and the photodetector 12 are separated a predetermined distance from the surface of the object OBJ. The surface pulse wave measurement unit 10 may measure a surface pulse wave of the object OBJ based on a change in the intensity of the light reflected from the surface of the object OBJ.

The light source 11 may use, for example, a light emitting diode (LED). In addition to the LED, various light emitting devices capable of emitting light may be used as the light source 11 without limitation. Also, there is no limit in the wavelength of the light radiated by the light source 11. A variety of photoelectric devices capable of detecting intensity of light may be employed as the photodetector 12. For example, the photodetector 12 may include a photodiode, a phototransistor, etc.

The guide portion 13 may include partitions 13a and 13b that are arranged vertically to fix the light source 11 and the photodetector 12. One end of each of the partitions 13a and 13b may be configured to protrude from a light emitting surface of the light source 11 and a light receiving surface of the photodetector 12. Accordingly, when the ends of the partitions 13a and 13b are in contact with the surface of the object OBJ, the light emitting surface of the light source 11 and the light receiving surface of the photodetector 12 may be spaced apart from the surface of the object OBJ. For example, a distance between the light emitting surface of the light source 11 or the light receiving surface of the photodetector 12 and the ends of the partitions 13a and 13b may be several millimeters, for example, about 1 mm to 10 mm.

Figure 2A:
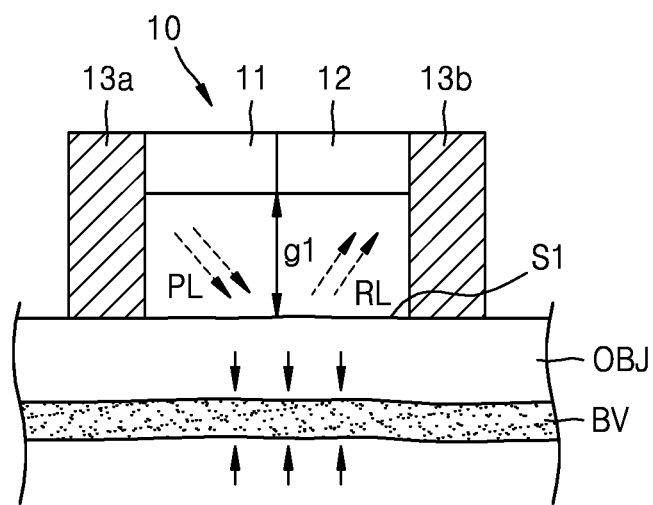
FIGS. 2A and 2B are cross-sectional views illustrating an operational principle of a surface pulse wave measurement unit.
Figure 2B:
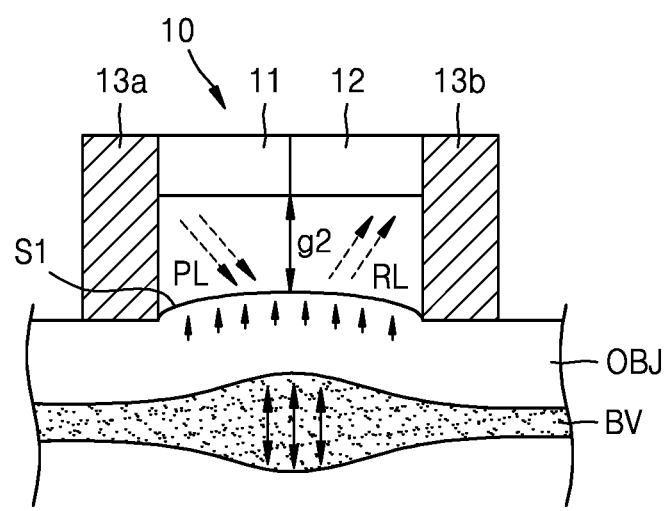

FIGS. 2A and 2B are cross-sectional views illustrating an operational principle of a surface pulse wave measurement unit. As illustrated in FIGS. 2A and 2B, light PL radiated by the light source 11 is reflected from the surface S1 of the object OBJ. Reflected light RL reflected from the surface S1 of the object OBJ is detected by the photodetector 12. The intensity of the reflected light RL detected by the photodetector 12 may be dependent upon a distance between the light source 11 or the photodetector 12 and the surface S1 of the object OBJ. For example, referring to FIG. 2A, during contraction of a blood vessel (BV), a gap g1 between the light source 11 or the photodetector 12 and the surface S1 of the object OBJ increases. In this state, the intensity of the reflected light RL detected by the photodetector 12 decreases. In contrast, referring to FIG. 2B, during relaxation of the blood vessel BV, as the blood vessel BV expands, the surface S1 of the object OBJ rises toward the light source 11 and the photodetector 12. Accordingly, a gap g2 between the light source 11 or the photodetector 12 and the surface S1 of the object OBJ decreases. In this state, the intensity of the reflected light RL detected by the photodetector 12 increases.

Figure 3:
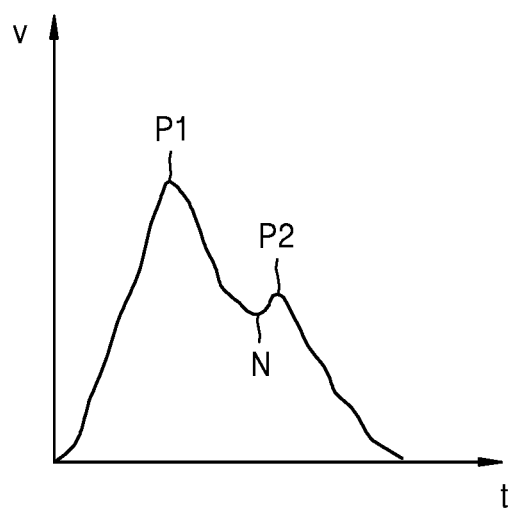
FIG. 3 is a graph illustrating an example of a surface pulse wave signal measured by the surface pulse wave measurement unit.

Accordingly, a degree of ascending/descending of the surface S1 of the object OBJ according to contraction/relaxation of the blood vessel BV may be seen by measuring the intensity of the reflected light RL through the photodetector 12, from which a surface pulse wave may be measured. For example, FIG. 3 is a graph illustrating an example of a surface pulse wave signal measured by the surface pulse wave measurement unit 10. In the graph of FIG. 3, a surface pulse wave signal may approximately match the intensity of the reflected light RL measured by the photodetector 12. However, the surface pulse wave signal of FIG. 3 may be obtained by shifting an intensity signal of the reflected light RL measured by the photodetector 12 in such a way that the amplitude of the surface pulse wave signal is zero "0" when the height of the surface S1 of the object OBJ is low, in other words, when the distance between the light source 11 or the photodetector 12 and the surface S1 of the object OBJ is the farthest during the contraction of the blood vessel BV.

FIGS. 1, 2A, and 2B schematically illustrate that the surface pulse wave measurement unit 10 includes one light source 11 and one photodetector 12. However, the surface pulse wave measurement unit 10 may be configured in various ways to improve accuracy in the measurement of a surface pulse wave.

Figure 4:
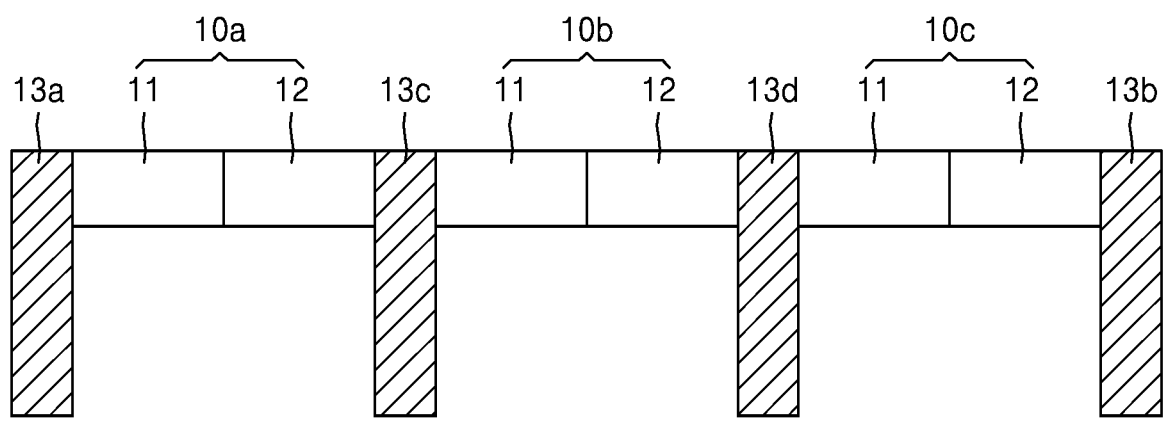
FIG. 4 is a cross-sectional view schematically illustrating a structure of a surface pulse wave measurement unit according to another exemplary embodiment.

FIG. 4 is a cross-sectional view schematically illustrating a structure of the surface pulse wave measurement unit according to another exemplary embodiment. Referring to FIG. 4, the surface pulse wave measurement unit 10 may include a plurality of light sources 11 and a plurality of photodetectors 12. Also, to reduce noise generated as the lights radiated by the plurality of light sources 11 are repeatedly reflected from the surface S1 of the object OBJ, each of the light sources 11 and each of the photodetectors 12 may be disposed close to each other, forming a first pair 10a of one of the light sources 11 and one of the photodetectors 12, a second pair 10b of another one of the light sources 11 and another one of the photodetectors 12, and a third pair 10c of another one of the light sources 11 and another one of the photodetectors 12. Also, to prevent crosstalk between the neighboring pairs 10a, 10b, and 10c of the light sources 11 and the photodetectors 12, the guide portion 13 may further include partitions 13c and 13d disposed between the neighboring pairs 10a, 10b, and 10c of the light sources 11 and the photodetectors 12. In this structure, an error in the measurement of a surface pulse wave may be reduced by averaging the intensity of the reflected light RL measured by using the (neighboring) pairs 10a, 10b, and 10c of the light sources 11 and the photodetectors 12.

Figure 5:
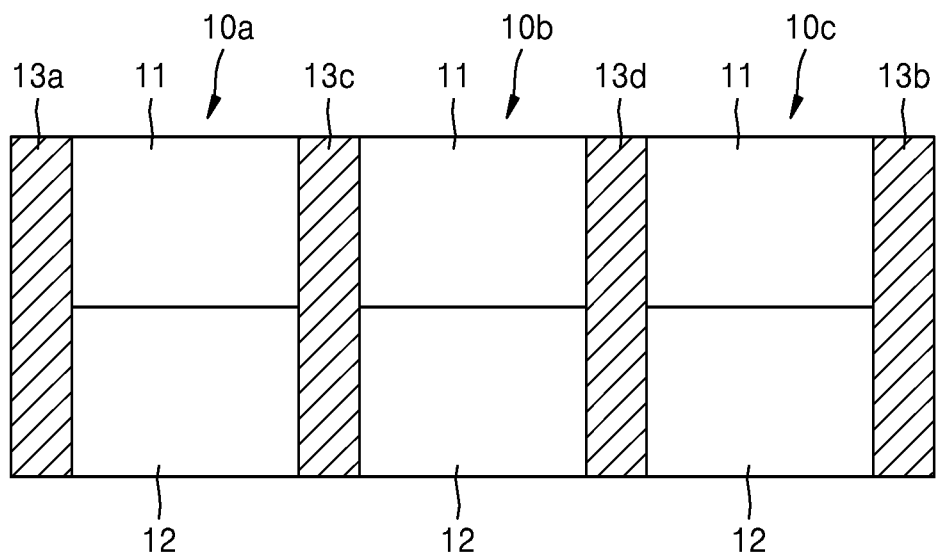
FIG. 5 is a plan view schematically illustrating a structure of a surface pulse wave measurement unit according to another exemplary embodiment.

FIG. 5 is a plan view schematically illustrating a structure of the surface pulse wave measurement unit according to another exemplary embodiment. In an example illustrated in FIG. 4, a plurality of pairs of the light source 11 and the photodetector 12 is sequentially disposed in a direction perpendicular to the surfaces of the partitions 13a, 13b, 13c, and 13d. In other words, an arrangement direction of the pairs 10a, 10b, and 10c and an arrangement direction of the light source 11 and the photodetector 12 may be identical to each other. In this case, the light source 11 and the photodetector 12, forming a pair, are fixed to two neighboring different partitions. In contrast, as illustrated in FIG. 5, the light source 11 and the photodetector 12, forming a pair, may be sequentially disposed in a direction along the surfaces of the partitions 13a, 13b, 13c, and 13d. Accordingly, the arrangement direction of the pairs 10a, 10b, and 10c and the arrangement direction of the light source 11 and the photodetector 12 may be perpendicular to each other. In this case, one partition may be disposed at each of both side surfaces of the light source 11 and the photodetector 12 that form a pair.

Figure 6A:
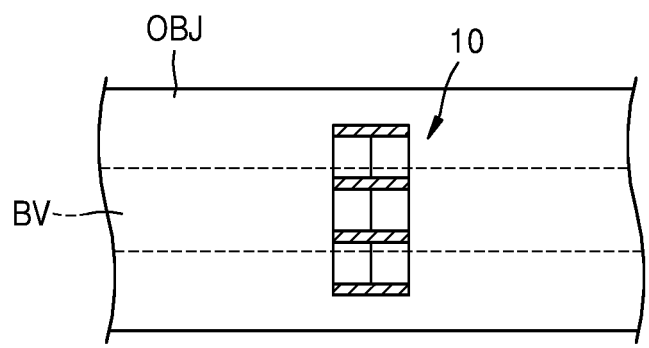
FIGS. 6A and 6B are plan views schematically illustrating an example of disposing a surface pulse wave measurement unit on an object.
Figure 6B:
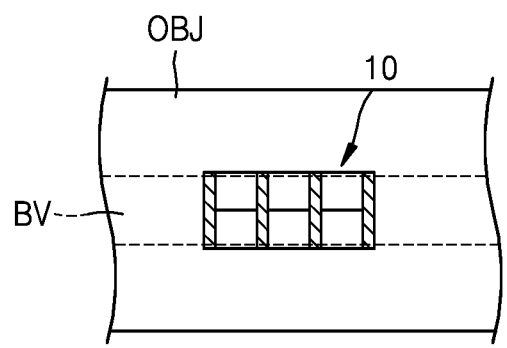

FIGS. 6A and 6B are plan views schematically illustrating an example of disposing the surface pulse wave measurement unit 10 of FIG. 5 on the object OBJ. In FIGS. 6A and 6B, a dotted line exemplarily shows a direction of the blood vessel BV inside the object OBJ. As illustrated in FIG. 6A, the surface pulse wave measurement unit 10 may be disposed such that the arrangement direction of the pairs 10a, 10b, and 10c and the direction of the blood vessel BV are perpendicular to each other. In this case, a surface pulse wave signal may be obtained by averaging the intensity of the reflected light RL measured by using the pairs 10a, 10b, and 10c. Also, as illustrated in FIG. 6B, the surface pulse wave measurement unit 10 may be disposed such that the arrangement direction of the pairs 10a, 10b, and 10c and the direction of the blood vessel BV are identical to each other. In this case, a pulse transit time (PTT) may be obtained by using a time difference between the pulse wave signals measured by the pairs 10a, 10b, and 10c disposed at different positions of the blood vessel BV.

Figure 7:
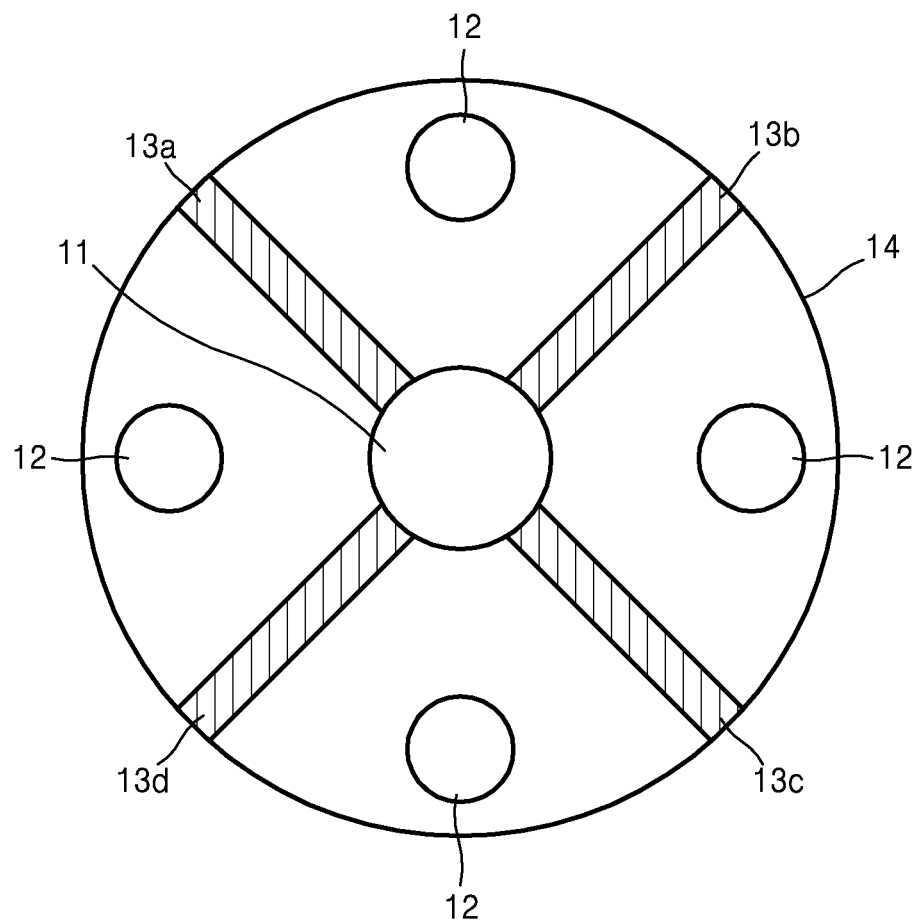
FIGS. 7 and 8 respectively are a bottom view and a perspective bottom view schematically illustrating a structure of a surface pulse wave measurement unit according to another exemplary embodiment.
Figure 8:
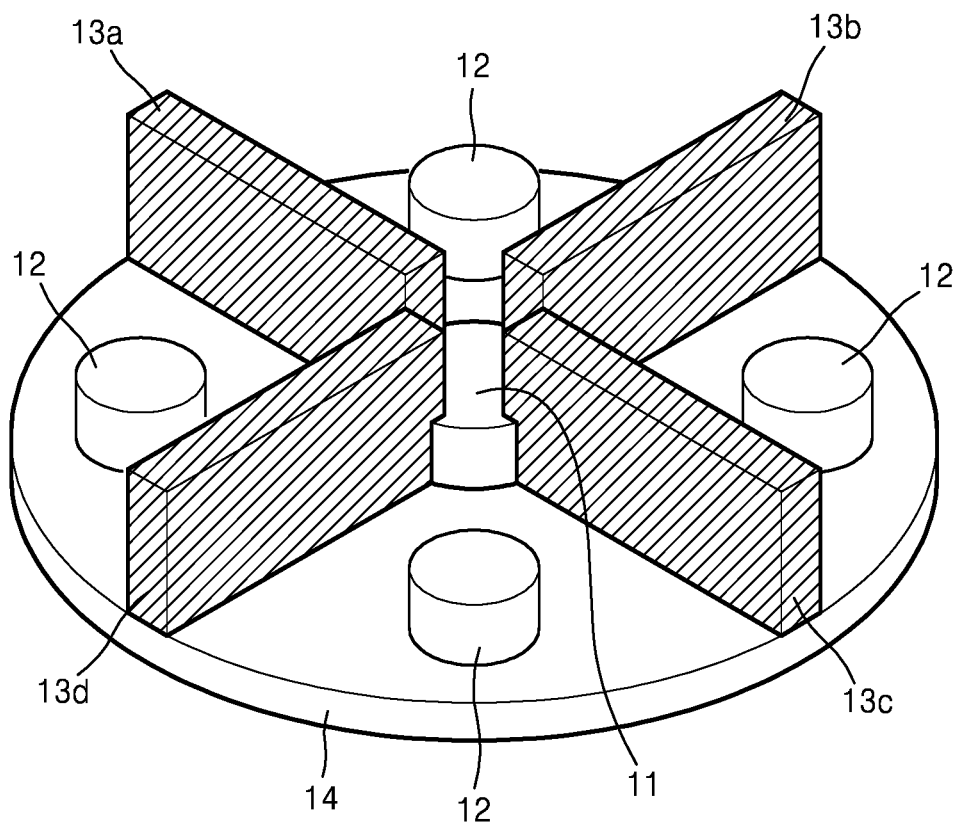

FIGS. 7 and 8 respectively are a bottom view and a perspective bottom view schematically illustrating a structure of the surface pulse wave measurement unit according to another exemplary embodiment. Although in the surface pulse wave measurement unit 10 of FIGS. 4 and 5, the pairs 10a, 10b, and 10c are linearly disposed, the surface pulse wave measurement unit may be configured to have a circular arrangement as illustrated in FIGS. 7 and 8. Referring to FIGS. 7 and 8, the surface pulse wave measurement unit 10 may include the light source 11 that is disposed at a center portion and the photodetectors 12 that are disposed along the circumference of the light source 11. Also, the guide portion may include the partitions 13a, 13b, 13c, and 13d that are disposed between the neighboring photodetectors 12. The partitions 13a, 13b, 13c, and 13d are disposed to protrude from the light emitting surface of the light source 11 and the light receiving surface of the photodetector 12. Although the photodetectors 12 may be directly fixed to and between the neighboring pair of the partitions 13a, 13b, 13c, and 13d, the photodetectors 12 may be fixed on a surface of the disk 14 on which the partitions 13a, 13b, 13c, and 13d are disposed. Although FIGS. 7 and 8 illustrate that only one light source 11 is disposed in the center portion, more than one light source 11 may be disposed in the center portion.

In the surface pulse wave measurement unit illustrated in FIGS. 4, 5, and 7, the light sources 11 and the photodetectors 12 may be operated simultaneously or sequentially. For example, by analyzing a signal to noise ratio of a detected optical signal while operating the pairs 10a, 10b, and 10c of the light source 11 and the photodetector 12 of FIGS. 4 and 5, or the photodetectors 12 of FIG. 7, one by one, any of the pairs 10a, 10b, and 10c or any of the photodetectors 12 that matches the blood vessel BV of the object OBJ may be found. Then, a surface pulse wave may be detected by using the pairs 10a, 10b, and 10c or the photodetector 12 disposed to match the blood vessel BV of the object OBJ. In this case, the surface pulse wave measurement unit 10 may measure a surface pulse wave of the object OBJ even when the pulse wave measurement unit 10 is not completely and accurately aligned with the blood vessel BV of the object OBJ, for example, a radial artery.

Figure 9:
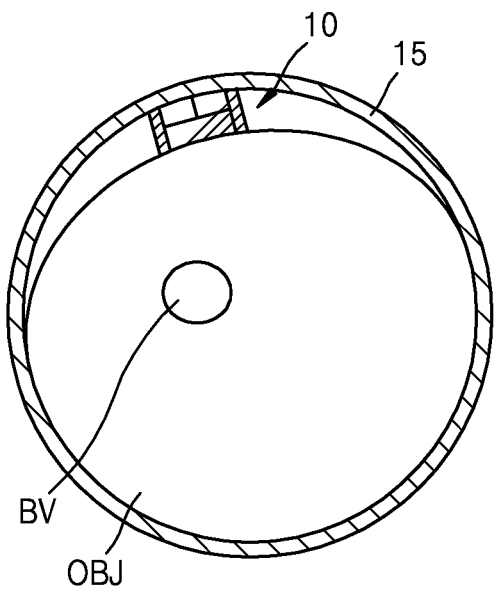
FIG. 9 is a cross-sectional view schematically illustrating an example in which a surface pulse wave measurement unit is worn on an object.

The surface pulse wave measurement unit may be connected to or included in various wearable devices such as a smart watch worn by the object OBJ, or health care related apparatuses or medical apparatuses. To this end, the apparatus 100, as illustrated in FIG. 9, may include a wearing unit configured to facilitate wearing of the surface pulse wave measurement unit 10 by the object OBJ. FIG. 9 is a cross-sectional view schematically illustrating an example in which the surface pulse wave measurement unit 10 is worn on the object OBJ. The wearing unit 15 of FIG. 9 may be embodied in various types, for example, a wristwatch type, a wristlet type, a wristband type, a ring type, a glasses type, or a hairband type, etc. FIG. 9 illustrates a simple example and a detailed shape of the wearing unit 15 is not limited to the example of FIG. 9. Also, although FIG. 9 illustrates that only the surface pulse wave measurement unit 10 is coupled to the wearing unit 15, the whole of the apparatus 100 of FIG. 1 may be coupled to the wearing unit 15.

Since the surface pulse wave measurement unit 10 adopts a method of simply measuring the intensity of the reflected light RL, for example, the light source 11 that is relatively inexpensive and incoherent, like an LED, and the photodetector 12 that is relatively inexpensive, like a photodiode, may be used.

Referring back to FIG. 1, the biometric signal extraction unit 30 may be configured to extract various biometric signal parameters based on a surface pulse wave of the object OBJ measured by the surface pulse wave measurement unit 10. For example, as shown in FIG. 1, the biometric signal extraction unit 30 may include a peak detection unit (e.g., peak detector) 31 that extracts a peak of a pulse wave signal, a dicrotic notch detection unit (e.g., dicrotic notch detector) 32 that extracts a dicrotic notch, a heart rate detection unit (e.g., heart rate detector) 33 that counts the number of pulse wave signals per unit time, and a pulse transit time detection unit (e.g., pulse transit time detector) 34 that extracts PTT between different points on the object OBJ.

The peak detection unit 31 may extract the amplitude and time of peaks P1 and P2 of the surface pulse wave signal of FIG. 3. The dicrotic notch detection unit 32 may extract the amplitude and time of a dicrotic notch N in the surface pulse wave signal of FIG. 3. The heart rate detection unit 33 may extract a heart rate by using a cycle of the surface pulse wave signal of FIG. 3. The pulse transit time detection unit 34 may extract a pulse transit time by using a time difference between the pulse wave signals measured by the pairs 10a, 10b, and 10c located at different positions on the blood vessel BV.

The analysis unit 40 may be configured to analyze various pieces of biometric information by using the various biometric signal parameters extracted by the biometric signal extraction unit 30. For example, by using a plurality of biometric signal parameters including the peak, dicrotic notch, heart rate, or pulse transit time of a pulse wave signal extracted by the biometric signal extraction unit 30, the analysis unit 40 may analyze the biometric information including blood vessel elasticity, a flow rate velocity, a degree of arteriosclerosis, a systolic blood pressure or diastolic blood pressure of a blood vessel, etc. Also, the biometric information may include information about whether a current blood pressure state is normal or abnormal.

The control unit 50 may control the surface pulse wave measurement unit 10 to measure the pulse wave signal, and may be configured to individually control the operations of the light sources 11 and the photodetectors 12. Also, the control unit 50 may control the biometric signal extraction unit 30 to extract a biometric signal parameter by using the pulse wave signal, and may control the analysis unit 40 to analyze the biometric information by using the biometric signal parameter. Although FIG. 1 illustrates the biometric signal extraction unit 30, the analysis unit 40, and the control unit 50 as separate blocks, the biometric signal extraction unit 30, the analysis unit 40, and the control unit 50 may be embodied, for example, by a single semiconductor processor chip or separate semiconductor processor chips. Alternatively, the biometric signal extraction unit 30, the analysis unit 40, and the control unit 50 may be embodied by software that is executable in a user's computer. For example, the biometric signal extraction unit 30 may be a software program that is stored in the memory 53 and executed by a computer to measure a surface pulse wave of the object OBJ.

Also, referring to FIG. 1, the apparatus 100 may further include a display unit (e.g., display) 51 that displays various biometric signal parameters extracted by the biometric signal extraction unit 30 or the pieces of the biometric information analyzed by the analysis unit 40, a command input unit 52 that inputs a user command, a memory 53 that stores the biometric signal parameters, the biometric information, or the user command, and a communication unit 54 that transmits an analysis result to other external devices.

The command input unit 52 may be embodied by a keypad, a touch screen, a voice recognition device, etc. The control unit 50 may control the surface pulse wave measurement unit 10, the biometric signal extraction unit 30, and the analysis unit 40 according to the user command input to the command input unit 52, and may display a result of the control on the display unit 51. The user may be an object of which biometric information is to be measured, that is, the object OBJ. However, the user may be a person, for example, a medical expert, who may use the apparatus 100 of the object OBJ.

The memory 53 may further store programs for the biometric signal extraction unit 30, the analysis unit 40, and the control unit 50. The memory 53 may include at least one of storage media, for example, flash memory, hard disk, multimedia card micro (MMC), card type memory, for example, SD or XD memory, random access memory (RAM), static random access memory (SRAM), read-only memory (ROM), electrically erasable programmable read-only memory (EEPROM), programmable read-only memory (PROM), magnetic memory, magnetic disk, optical disk, etc.

An external device communicating with the communication unit 54 may be, for example, medical equipment using the analyzed biometric information or a printer for printing a result. In addition, the external device may be smartphones, mobile phones, personal digital assistants (PDAs), laptop computers, personal computers (PCs), and other mobile or non-mobile computing devices, but not limited thereto.

The communication unit 54 may be connected to the external device by wire or wirelessly. For example, the communication unit 54 may communicate with the external device by using a method, for example, Bluetooth communication, Bluetooth low energy (BLE) communication, near field communication (NFC), wireless local area network (WLAN) or WIFI communication, Zigbee communication, infrared data association (IrDA) communication, Wi-Fi direct (WFD) communication, ultra wideband (UWB) communication, Ant+ communication, WIFI communication, etc., but not limited thereto.

Figure 10:
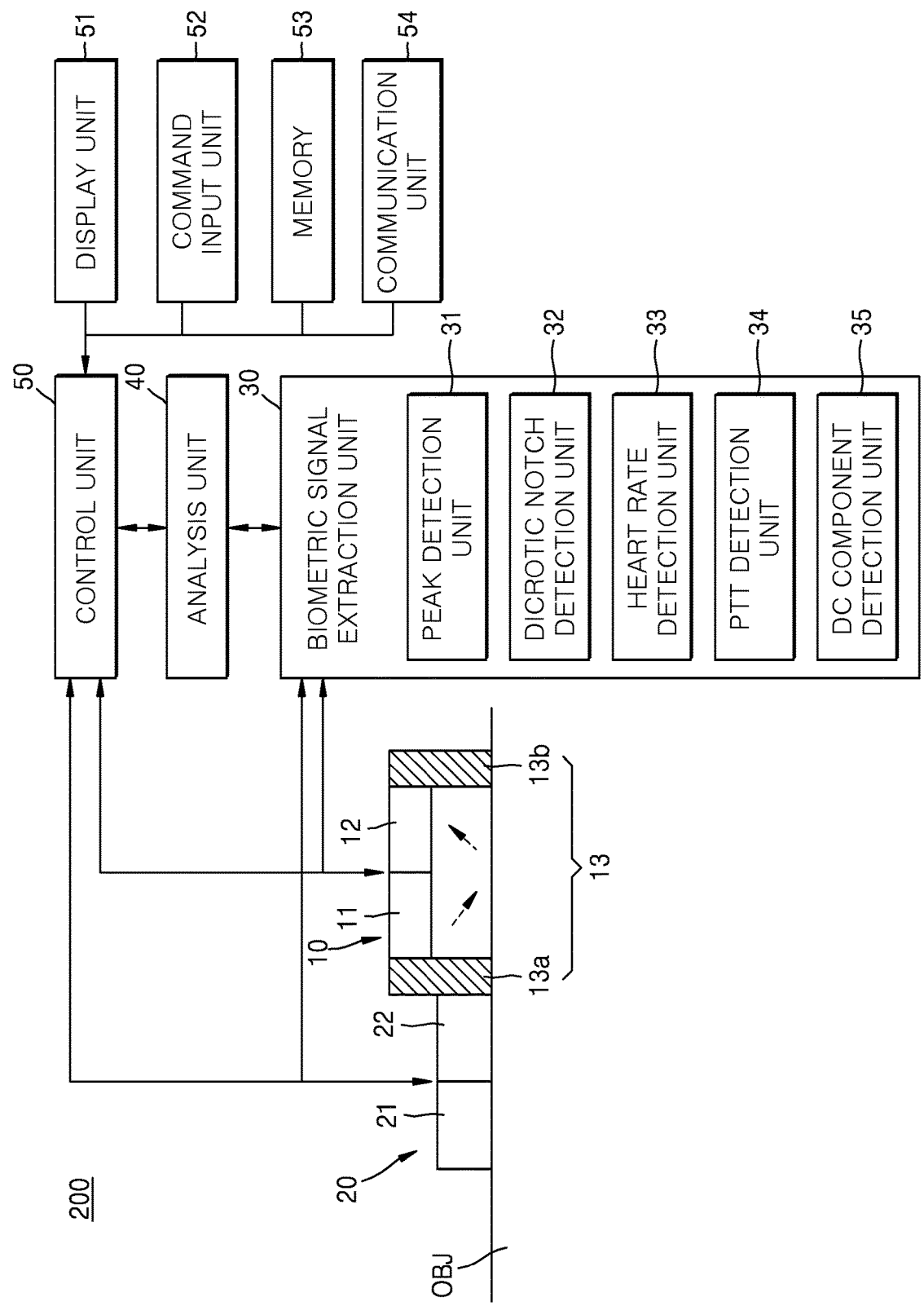
FIG. 10 is a block diagram schematically illustrating a structure of an apparatus for detecting biometric information according to another exemplary embodiment.

FIG. 10 is a block diagram schematically illustrating a structure of an apparatus 200 for detecting biometric information according to another exemplary embodiment. Referring to FIG. 10, the apparatus 200 may include the surface pulse wave measurement unit 10 disposed on the surface of the object OBJ and optically measuring a surface pulse wave of the object OBJ, a photo-plethysmogram (PPG) measurement unit 20 that measures a PPG of the object OBJ, and the biometric signal extraction unit 30 that extracts a plurality of biometric signal parameters based on the surface pulse wave of the object OBJ measured by the surface pulse wave measurement unit 10 and the PPG of the object OBJ measured by the PPG measurement unit 20. Also, the apparatus 200 may further include the analysis unit 40 that analyzes biometric information by using the various biometric signal parameters extracted by the biometric signal extraction unit 30, the control unit 50 that controls the operations of the surface pulse wave measurement unit 10, the biometric signal extraction unit 30, and the analysis unit 40, the display unit 51, the command input unit 52, the memory 53, and the communication unit 54.

Compared to the apparatus 100 of FIG. 1, the apparatus 200 of FIG. 10 may further include the PPG measurement unit 20 that measures the PPG of the object OBJ. The apparatus 200 according to the present exemplary embodiment may detect biometric information by using both of the surface pulse wave of the object OBJ measured by the surface pulse wave measurement unit 10 and the PPG of the object OBJ measured by the PPG measurement unit 20. The other structure of the apparatus 200 may be the same as or similar to the structure of the apparatus 100 of FIG. 1.

As illustrated in FIG. 10, the surface pulse wave measurement unit 10 and the PPG measurement unit 20 may be used together by being combined with each other. For example, the surface pulse wave measurement unit 10 and the PPG measurement unit 20 both may be fixed to the guide portion 13. As described above, the surface pulse wave measurement unit 10 may include the light source 11 that radiates incoherent light and the photodetector 12 that measures the intensity of light radiated by the light source 11 and reflected from the surface of the object OBJ. The light source 11 and the photodetector 12 of the surface pulse wave measurement unit 10 may be fixed to the guide portion 13 to be separated from the surface of the object OBJ.

The PPG measurement unit 20 may measure PPG by using characteristics that blood, in particular, a red cell, well absorbs light of a red or infrared range. For example, the PPG measurement unit 20 may include a light source 21 that radiates light of a red or near-infrared range and a photodetector 22 that measures the intensity of light of a red or near-infrared range. The light source 21 may be disposed in contact with the surface of the object OBJ so that light may easily intrude into the blood vessel BV inside the object OBJ. Also, the photodetector 22 may be disposed in contact with the surface of the object OBJ, to easily detect light that is absorbed in the blood of the object OBJ and then re-radiated therefrom. To this end, the light source 21 and the photodetector 22 of the PPG measurement unit 20 may be fixed to the guide portion 13 to closely contact the surface of the object OBJ. For example, the light source 11 and the photodetector 12 of the surface pulse wave measurement unit 10 may be fixed on an upper area of the guide portion 13, whereas the light source 21 and the photodetector 22 of the PPG measurement unit 20 may be fixed on a lower area of the guide portion 13.

The surface pulse wave measurement unit 10 may use any type of a light-emitting body as the light source 11. Also, the type of the photodetector 12 of the surface pulse wave measurement unit 10 is not limited. Accordingly, for convenience of assembly, the light source 11 and the photodetector 12 of the surface pulse wave measurement unit 10 may be respectively the same as the light source 21 and the photodetector 22 of the PPG measurement unit 20. For example, the light source 11 and the photodetector 12 of the surface pulse wave measurement unit 10 may radiate and detect light in a red or near-infrared range. In this case, the surface pulse wave measurement unit 10 and the PPG measurement unit 20 may be distinguished by a relative position to the surface of the object OBJ.

The biometric signal extraction unit 30 of the apparatus 200 of FIG. 10 may include, for example, the peak detection unit 31 that extracts a peak of a pulse wave signal, the dicrotic notch detection unit 32 that extracts a dicrotic notch, the heart rate detection unit 33 that counts the number of pulse wave signals per unit time, the pulse transit time detection unit 34 that extracts PTT between different points on the object OBJ, and a direct current (DC) component detection unit 35 that extracts a DC component of a PPG signal. The DC component may be referred to as a non-pulsatile component which does not vary with blood pressure. In other words, the DC component may not change on a beat to beat basis. The peak detection unit 31, the dicrotic notch detection unit 32, the heart rate detection unit 33, and the pulse transit time detection unit 34 may extract the biometric signal parameters by using both of the surface pulse wave measured by the surface pulse wave measurement unit 10 and the PPG measured by the PPG measurement unit 20. The DC component detection unit 35 may extract a DC component of a PPG signal by using the PPG measured by the PPG measurement unit 20.

The analysis unit 40 may be configured to analyze various pieces of biometric information by using the various biometric signal parameters extracted by the biometric signal extraction unit 30. For example, the analysis unit 40 may analyze the biometric information including blood vessel elasticity, a flow rate velocity, a degree of arteriosclerosis, a systolic blood pressure or diastolic blood pressure of a blood vessel, etc. by using the biometric signal parameters including the peak, dicrotic notch, heart rate, pulse transit time, or DC component of a PPG signal of the pulse wave signal extracted by the biometric signal extraction unit 30.

In an example of FIG. 10, the light source 11 and the photodetector 12 of the surface pulse wave measurement unit 10 may be disposed forming a pair and close to each other, and the light source 21 and the photodetector 22 of the PPG measurement unit 20 may also be disposed forming a pair and close to each other. The guide portion 13 may include a first partition 13a disposed between the pair of the light source 11 and the photodetector 12 of the surface pulse wave measurement unit 10 and the pair of the light source 21 and the photodetector 22 of the PPG measurement unit 20, and a second partition 13b disposed at the photodetector 12 of the surface pulse wave measurement unit 10. Also, the light source 21 and the photodetector 22 of the PPG measurement unit 20, and the light source 11 and the photodetector 12 of the surface pulse wave measurement unit 10 are sequentially and linearly disposed in a direction perpendicular to the surfaces of the first and second partitions 13a and 13b. For example, the photodetector 22 may be fixed on a left surface of the first partition 13a and the light source 21 may be disposed at a left side of the photodetector 22. Also, the light source 11 may be fixed on a right surface of the first partition 13a and the photodetector 12 may be disposed at a right side of the light source 11. However, the structures of the surface pulse wave measurement unit 10 and the PPG measurement unit 20 are not limited to the example of FIG. 10 and may be formed in a variety of ways.

Figure 11A:
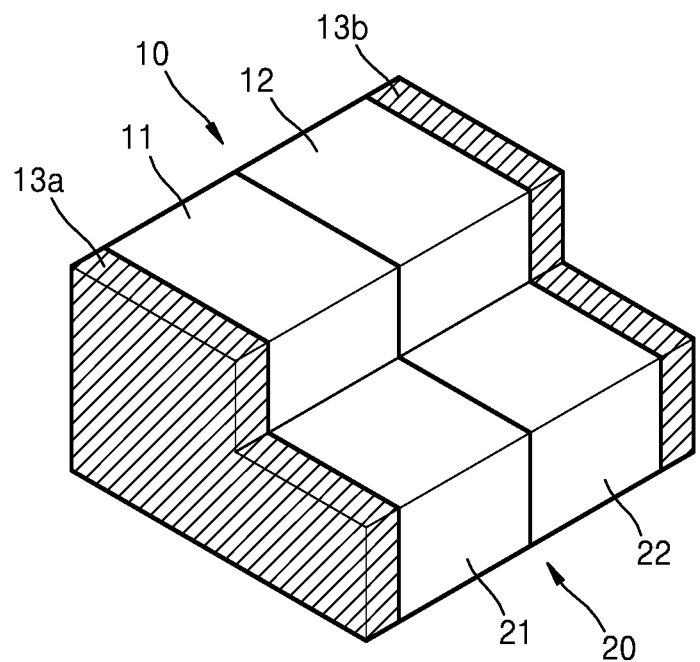
FIGS. 11A and 11B are perspective views schematically illustrating structures of a surface pulse wave measurement unit and photo-plethysmogram measurement unit.
Figure 11B:
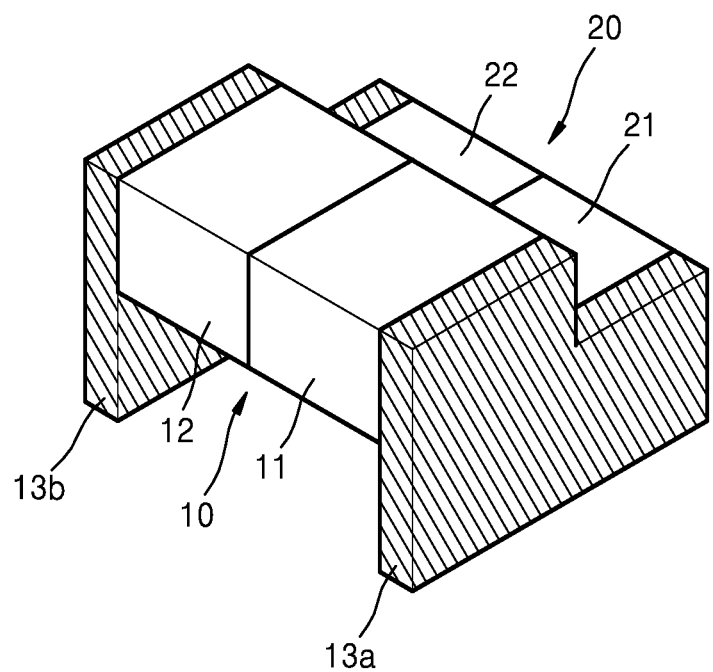

For example, FIGS. 11A and 11B are, respectively, front and rear perspective views schematically illustrating structures of the surface pulse wave measurement unit 10 and the PPG measurement unit 20 according to another exemplary embodiment. Referring to FIGS. 11A and 11B, the surface pulse wave measurement unit 10 and the PPG measurement unit 20 may be fixed together between the partitions 13a and 13b of the guide portion 13. For example, the light source 11 of the surface pulse wave measurement unit 10 and the light source 21 of the PPG measurement unit 20 may be fixed on a right surface of the first partition 13a. The photodetector 12 of the surface pulse wave measurement unit 10 and the photodetector 22 of the PPG measurement unit 20 may be fixed on a left surface of the second partition 13b. The PPG measurement unit 20 may be disposed on a front surface of the guide portion 13 and the surface pulse wave measurement unit 10 may be disposed on a rear surface of the guide portion 13.

Also, the PPG measurement unit 20 may be disposed on a lower area of the guide portion 13 and the surface pulse wave measurement unit 10 may be disposed on an upper area of the guide portion 13. In other words, as illustrated in FIG. 11A, a light emitting surface of the light source 21 and a light receiving surface of the photodetector 22 of the PPG measurement unit 20 are disposed matching lower surfaces of the first and second partitions 13a and 13b. In contrast, as illustrated in FIG. 11B, an upper surface of the light source 11 and an upper surface of the photodetector 12 of the surface pulse wave measurement unit 10 may be disposed matching upper surfaces of the first and second partitions 13a and 13b. Accordingly, when the guide portion 13 is located at the object OBJ, the PPG measurement unit 20 may contact the surface of the object OBJ and the surface pulse wave measurement unit 10 may be separated from the surface of the object OBJ.

Figure 12:
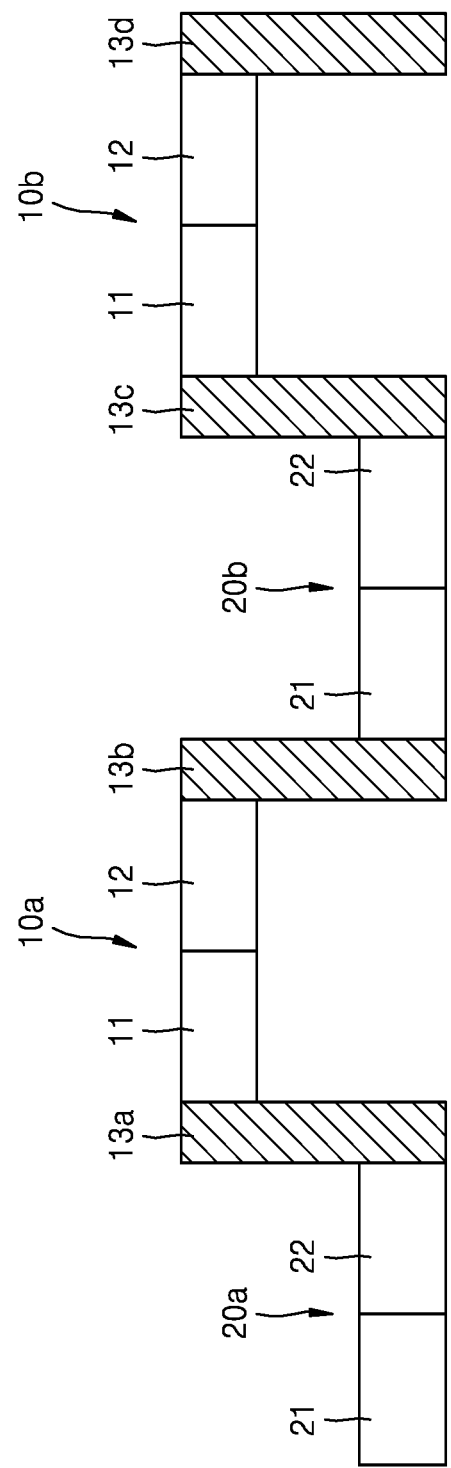
FIG. 12 is a cross-sectional view schematically illustrating a structure of a surface pulse wave measurement unit and a photo-plethysmogram measurement unit according to another exemplary embodiment.

FIG. 12 is a cross-sectional view schematically illustrating a structure of the surface pulse wave measurement unit 10 and the PPG unit 20 according to another exemplary embodiment. Referring to FIG. 12, the surface pulse wave measurement unit 10 may include a plurality of pairs, each including one light source 11 and one photodetector 12. The PPG measurement unit 20 may include a plurality of pairs 20a and 20b, each including one light source 21 and one photodetector 22. The pairs 10a and 10b of the surface pulse wave measurement unit 10 and the pairs 20a and 20b of the PPG measurement unit 20 may be alternately disposed one by one so that one pair 10a or 10b of the surface pulse wave measurement unit 10 and one pair 20a or 20b of the PPG measurement unit 20 are disposed to neighbor each other. The guide portion 13 may include first to third partitions 13a, 13b, and 13c which are respectively disposed between the pairs 10a and 10b of the surface pulse wave measurement unit 10 and the pairs 20a and 20b of the PPG measurement unit 20. Also, the guide portion 13 may further include a fourth partition 13d that fixed the pair 10b of the surface pulse wave measurement unit 10. As illustrated in FIG. 12, the pairs 10a and 10b of the surface pulse wave measurement unit 10 may be fixed on upper portions of the first to fourth partitions 13a, 13b, 13c, and 13d, and the pairs 20a and 20b of the PPG measurement unit 20 may be fixed to lower portions of the first to third partitions 13a, 13b, and 13c.

Figure 13:
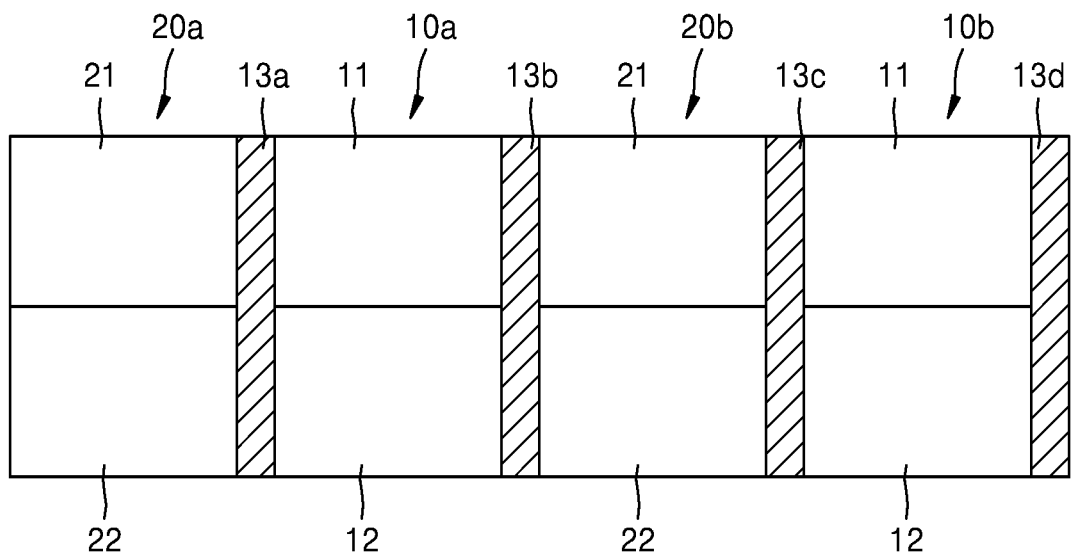
FIG. 13 is a plan view schematically illustrating a structure of a surface pulse wave measurement unit and a photo-plethysmogram measurement unit according to another exemplary embodiment.

FIG. 13 is a plan view schematically illustrating a structure of the surface pulse wave measurement unit 10 and the photo-plethysmogram measurement unit 20 according to another exemplary embodiment. In the example illustrated in FIG. 12, the light source 21 and the photodetector 22 of the PPG measurement unit 20, and the light source 11 and the photodetector 12 of the surface pulse wave measurement unit 10, are sequentially and linearly disposed in a direction perpendicular to the surfaces of the first to fourth partitions 13a, 13b, 13c, and 13d. In contrast, as illustrated in FIG. 13, the light source 11 and the photodetector 12 of the surface pulse wave measurement unit 10, forming one pair 10a or 10b, may be sequentially disposed in a direction along the surfaces of the first to fourth partitions 13a, 13b, 13c, and 13d. Likewise, the light source 21 and the photodetector 22 of the PPG measurement unit 20, forming one pair 20a or 20*b*, may be sequentially disposed in a direction along the surfaces of the first to third partitions 13*a*, 13*b*, and 13*c*. In the example illustrated in FIG. 13, the pairs 10*a* and 10*b* of the surface pulse wave measurement unit 10 and the pairs 20*a* and 20*b* of the PPG measurement unit 20 may be alternately disposed. Also, although not illustrated in FIG. 13, the pairs 10*a* and 10*b* of the surface pulse wave measurement unit 10 may be fixed on upper portions of the first to fourth partitions 13*a*, 13*b*, 13*c*, and 13*d*, and the pairs 20*a* and 20*b* of the PPG measurement unit 20 may be fixed on lower portions of the first to third partitions 13*a*, 13*b*, and 13*c* as in FIG. 12.

Also, in the example of FIG. 13, the first to third partitions 13*a*, 13*b*, and 13*c* that are disposed between the pairs 10*a* and 10*b* of the surface pulse wave measurement unit 10 and the pairs 20*a* and 20*b* of the PPG measurement unit 20 may not be used. Instead, one partition that fixes both of the light sources 11 and 21 of the surface pulse wave measurement unit 10 and the PPG measurement unit 20 and another partition that fixes both of the photodetectors 12 and 22 of the surface pulse wave measurement unit 10 and the PPG measurement unit 20, in the form illustrated FIGS. 11A and 11B, may be used. In other words, the surface pulse wave measurement unit 10 and the PPG measurement unit 20 illustrated in FIGS. 11A and 11B may be disposed in a plurality of pairs.

Figure 14:
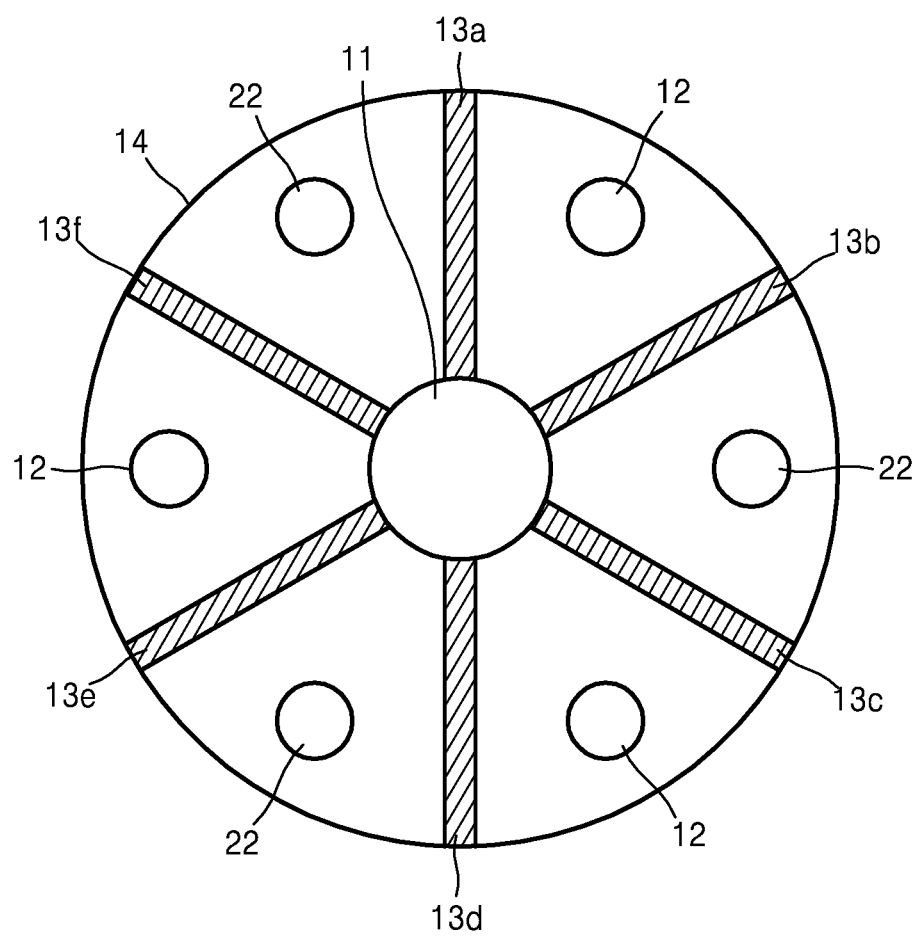
FIG. 14 is a bottom view schematically illustrating a structure of a surface pulse wave measurement unit and a photo-plethysmogram measurement unit according to another exemplary embodiment.

FIG. 14 is a bottom view schematically illustrating a structure of the surface pulse wave measurement unit and the photo-plethysmogram measurement unit according to another exemplary embodiment. Referring to FIG. 14, the photodetectors 12 of the surface pulse wave measurement unit 10 and the photodetector 22 of the PPG measurement unit 20 may be disposed around the light source 11. The light source 11 may radiate light of a red or near-infrared range. The photodetectors 12 of the surface pulse wave measurement unit 10 and the photodetector 22 of the PPG measurement unit 20 may be alternately disposed in a direction along the circumference of the light source 11. Although FIG. 14 illustrates that only one light source 11 is disposed at a center portion, the plurality of light sources 11 may be disposed at the center portion thereof.

Also, the guide portion 13 may include a plurality of partitions 13*a*, 13*b*, 13*c*, 13*d*, 13*e*, and 13*f* respectively disposed between the neighboring photodetectors 12 and 22. The photodetectors 12 and 22 may be directly fixed to and between the neighboring two of the partitions 13*a*, 13*b*, 13*c*, 13*d*, 13*e*, and 13*f*, or may be fixed on the surface of the disc 14 on which the partitions 13*a*, 13*b*, 13*c*, 13*d*, 13*e*, and 13*f* are disposed. When the disc 14 is in use, the disc 14 may have a plurality of areas having different heights such that the photodetector 12 of the surface pulse wave measurement unit 10 is separated from the surface of the object OBJ and the photodetector 22 of the PPG measurement unit 20 contacts the surface of the object OBJ. For example, the height of an area of the disc 14 where the photodetector 22 of the PPG measurement unit 20 is disposed may be low and the height of an area of the disc 14 where the photodetectors 12 of the surface pulse wave measurement unit 10 is disposed may be high.

According to the present embodiment, biometric information like a blood pressure may be more accurately extracted by detecting the surface pulse wave and PPG together by using the surface pulse wave measurement unit 10 and the PPG measurement unit 20. For example, since light that is directly reflected from the surface of the object OBJ is used by the surface pulse wave measurement unit 10, a high signal to noise ratio may be obtained. Also, since the PPG measurement unit 20 may extract a DC component that depends upon the diameter of the blood vessel BV of the object OBJ, an error due to a diametric deviation between the blood vessels BVs of the objects OBJs may be prevented or reduced.

Figure 15A:
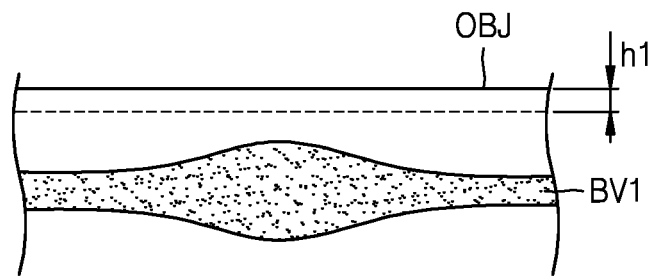
FIGS. 15A and 15B are cross-sectional views schematically illustrating diastole and systole of a blood vessel when the diameter of the blood vessel is relatively small.
Figure 15B:
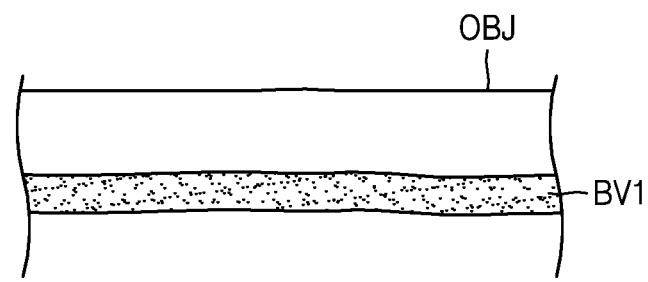
Figure 16A:
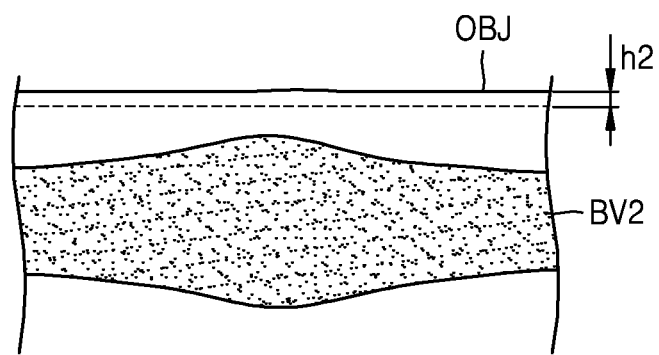
FIGS. 16A and 16B are cross-sectional views schematically illustrating diastole and systole of a blood vessel when the diameter of the blood vessel is relatively large.
Figure 16B:
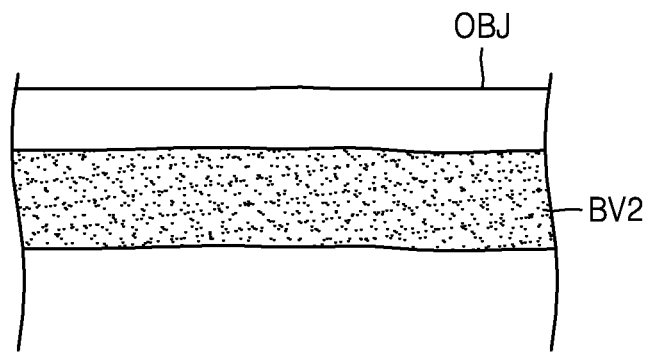

FIGS. 15A and 15B are cross-sectional views schematically illustrating diastole and systole of a blood vessel when the diameter of the blood vessel is relatively small. FIGS. 16A and 16B are cross-sectional views schematically illustrating diastole and systole of a blood vessel when the diameter of the blood vessel is relatively large. Referring to FIGS. 15A and 15B, for a blood vessel BV1 having a relatively small diameter during a systolic period, an amount of an increase in the diameter of the blood vessel BV1 during diastolic period is relatively large. Accordingly, an amount h1 of an increase in the height of the surface of the object OBJ is high during a diastolic period. In contrast, referring to FIGS. 16A and 16B, for a blood vessel BV2 having a relatively large diameter during the systolic period, an amount of an increase in the diameter of the blood vessel BV2 during the diastolic period is relatively small. Accordingly, an amount h2 of an increase in the height of the surface of the object OBJ is small during relaxation. In other words, h1>h2. The diameter of a blood vessel during the systolic period differs person to person.

Figure 17:
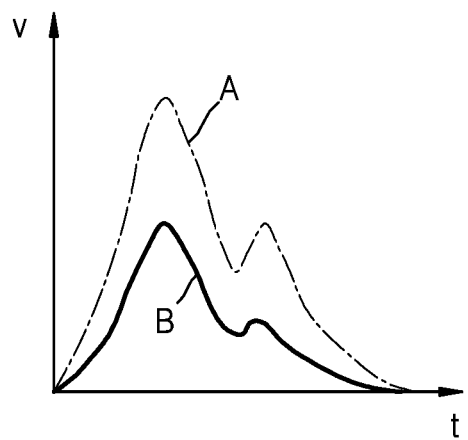
FIG. 17 is a graph showing an example of a surface pulse wave signal measured by the surface pulse wave measurement unit.

As such, the amplitude of a surface pulse wave measured with respect to the blood vessel BV2 having a diameter that is large during the systolic period is smaller than the amplitude of a surface pulse wave measured with respect to the blood vessel BV1 having a diameter that is small during the systolic period. For example, FIG. 17 is a graph showing an example of a surface pulse wave signal measured by the surface pulse wave measurement unit. In the graph of FIG. 17, a graph A indicated by a dot-dash line denotes a surface pulse wave signal measured with respect to the blood vessel BV1 having a diameter that is relatively small during the systolic period, and a graph B indicated by a solid line denotes a surface pulse wave signal measured with respect to the blood vessel BV2 having a diameter that is relatively large during the systolic period. As illustrated in FIG. 17, the surface pulse wave signal measured with respect to the blood vessel BV1 having a diameter that is relatively small during the systolic period has an amplitude that is larger than that of the surface pulse wave signal measured with respect to the blood vessel BV2 having a diameter that is relatively large during the systolic period. Accordingly, when a blood pressure is obtained with only the amplitude of the surface pulse wave signal, an error may occur because an individual difference in the diameter of a blood vessel is not reflected.

Figure 18:
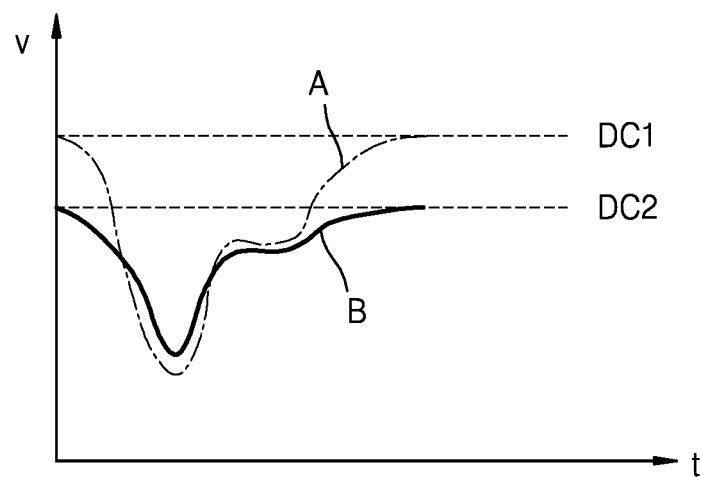
FIG. 18 is a graph showing an example of a photo-plethysmogram signal measured by the photo-plethysmogram measurement unit.

FIG. 18 is a graph showing an example of a PPG signal measured by the PPG measurement unit 20. In the graph of FIG. 18, a graph A indicated by a dot-dash line denotes a PPG signal measured with respect to the blood vessel BV1 having a diameter that is relatively small during the systolic period, and a graph B indicated by a solid line denotes a PPG signal measured with respect to the blood vessel BV2 having a diameter that is relatively large during the systolic period. As illustrated in FIG. 18, the PPG measurement unit 20 that measures the intensity of light that is left after being absorbed in blood in a blood vessel may obtained a PPG signal having DC components DC1 and DC2 that depend on the diameters of the blood vessels BV1 and BV2. For example, a PPG signal measured with respect to the blood vessel BV1 having a diameter that is relatively small during the systolic period has a relatively large DC component DC1, and a PPG signal measured with respect to the blood vessel BV2 having a diameter that is relatively large during the systolic period has a relatively small DC component DC2. Also, the PPG signal measured with respect to the blood vessel BV1 having a diameter that is relatively small during the systolic period has an amplitude that is larger than that of the PPG signal measured with respect to the blood vessel BV2 having a diameter that is relatively large during the systolic period.

Accordingly, a diameter of a blood vessel may be estimated by using the amount of a DC component of a PPG signal. Then, by compensating for the amount of a blood pressure estimated by using a change in the amplitudes of the surface pulse wave signal and the PPG signal, considering the amount of a DC component, an accurate blood pressure of the object OBJ may be calculated. In particular, since a signal to noise ratio of the surface pulse wave measurement unit is high, the accuracy of measuring a blood pressure may be further improved.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for detecting biometric information, the apparatus comprising:
   a surface pulse wave measurement unit configured to obtain a surface pulse wave of an object, the surface pulse wave measurement unit comprising:
   at least one light source configured to radiate light to a surface of the object while the surface pulse wave measurement unit is spaced apart from the surface of the object;
   at least one photodetector configured to measure an intensity of light radiated by the at least one light source and reflected from the surface of the object while the surface pulse wave measurement unit is spaced apart from the surface of the object; and
   a photo-plethysmogram (PPG) signal measurement unit comprising at least one light source and at least one photodetector, and configured to obtain a PPG signal of the object while at least one light source and at least one photodetector of the PPG signal measurement unit are in contact with the surface of the object;
   a guide portion comprising a partition that comprises a first surface and a second surface that oppose each other and are disposed in parallel with a contact surface of the PPG signal measurement unit, and comprises a first side surface and a second side surface that are perpendicular to the first surface and the second surface, and extend from the first surface to the second surface, so that the first side surface and the second side surface of the partition of the guide portion are disposed perpendicular to the surface of the object when the contact surface of the PPG signal measurement unit is contacted with the surface of the object, the guide portion being configured to fix the at least one light source and the at least one photodetector of the surface pulse wave measurement unit to an upper portion of the first side surface of the partition so that the surface pulse wave measurement unit is configured to be spaced apart from the surface of the object while the surface pulse wave measurement unit is obtaining the surface pulse wave of the object, and fix the at least one light source and the at least one photodetector of the PPG signal measurement unit to a lower portion of the second side surface of the partition so that the PPG signal measurement unit is configured to be in contact with the surface of the object while the PPG signal measurement unit is obtaining the PPG signal of the object, the first side surface of the partition being disposed to oppose the second side surface of the partition; and
   a biometric signal extractor configured to extract a plurality of biometric signal parameters based on the surface pulse wave and the PPG signal of the object,
   wherein the lower portion of the second side surface of the partition is configured to be disposed closer to the surface of the object than the upper portion of the first die surface of the partition.

2. The apparatus of claim 1, wherein the at least one light source and the at least one photodetector of the surface pulse wave measurement unit are disposed adjacently to and in contact with each other to form a first pair such that the surface pulse wave measurement unit is configured to measure a degree of ascending/descending of the surface of the object according to contraction/relaxation of a blood vessel based on the intensity of the light reflected by the surface of the object,
   wherein the at least one light source and the at least one photodetector of the PPG signal measurement unit are disposed adjacently to and in contact with each other to form a second pair, and
   wherein the degree of ascending/descending of the surface of the object is represented by a distance between the surface pulse wave measurement unit and the surface of the object.

3. The apparatus of claim 1, wherein the surface pulse wave measurement unit is disposed in parallel with the PPG measurement unit.

4. The apparatus of claim 3, wherein the surface pulse wave measurement unit and the PPG measurement unit are disposed to radiate the light in a same direction.

5. The apparatus of claim 1, wherein the biometric signal extractor comprises:
   a peak detector configured to extract a peak of the surface pulse wave;
   a dicrotic notch detector configured to extract a dicrotic notch of the surface pulse wave;

a heart rate detector configured to count a number of a plurality of surface pulse waves per unit time, the plurality of surface pulse waves comprising the surface pulse wave; and a pulse time detector configured to extract a pulse transit time (PTT) of the surface pulse wave between at least two different positions on the object.

6. The apparatus of claim 5, further comprising an analyzer configured to analyze biometric information including blood vessel elasticity, a flow rate velocity, a degree of arteriosclerosis, a systolic blood pressure, or a diastolic blood pressure of a blood vessel, based on the plurality of biometric signal parameters including the peak, the dicrotic notch, a heart rate, or the PTT.

7. An apparatus for detecting biometric information, the apparatus comprising:

a surface pulse wave measurement unit comprising:

at least one first light source configured to radiate a first light to a surface of an object while the surface pulse wave measurement unit is spaced apart from the surface of the object; and at least one first photodetector configured to obtain a surface pulse wave by measuring an intensity of the first light reflected from the surface of the object while the surface pulse wave measurement unit is spaced apart from the surface of the object; and a photo-plethysmogram (PPG) measurement unit comprising:

at least one second light source configured to radiate a second light to the surface of the object while the PPG measurement unit is in contact with the surface of the object; and at least one second photodetector configured to obtain a PPG signal by measuring an intensity of the second light reflected from the surface of the object while the PPG measurement unit is in contact with the surface of the object; and a biometric signal extractor configured to extract a plurality of biometric signal parameters based on the surface pulse wave and the PPG signal measured by the PPG measurement unit; and a guide portion comprising a partition that comprises a first surface and a second surface that oppose each other and are disposed in parallel with a contact surface of the PPG signal measurement unit, and comprises a first side surface and a second side surface that are perpendicular to the first surface and the second surface, and extend from the first surface to the second surface, so that the first side surface and the second side surface of the partition of the guide portion are disposed perpendicular to the surface of the object when the contact surface of the PPG signal measurement unit is contacted with the surface of the object, and configured to fix the at least one first light source and the at least one first photodetector of the surface pulse wave measurement unit to an upper portion of the first side surface of the partition so that the surface pulse wave measurement unit is configured to be spaced apart from the surface of the object while the surface pulse wave measurement unit is obtaining the surface pulse wave of the object, and fix the at least one second light source and the at least one second photodetector of the PPG signal measurement unit to a lower portion of the second side surface of the partition so that the PPG signal measurement unit is configured to be in contact with the surface of the object while the PPG signal measurement unit is obtaining the PPG signal of the object, the first side surface of the partition being disposed to oppose the second side surface of the partition, wherein the lower portion of the second side surface of the partition is configured to be disposed closer to the surface of the object than the upper portion of the first side surface of the partition, wherein the lower portion of the second side surface of the partition is configured to be disposed closer to the surface of the object than the upper portion of the first side surface of the partition.

8. The apparatus of claim 7, wherein the at least one first light source and the at least one first photodetector of the surface pulse wave measurement unit are disposed adjacently to and in contact with each other to form a first pair such that the surface pulse wave measurement unit is configured to measure a degree of ascending/descending of the surface of the object according to contraction/relaxation of a blood vessel based on the intensity of the first light reflected by the surface of the object, and wherein the at least one second light source and the at least one second photodetector of the PPG measurement unit are disposed adjacently to and in contact with each other to form a second pair, and wherein the degree of ascending/descending of the surface of the object is represented by a distance between the surface pulse wave measurement unit and the surface of the object.

9. The apparatus of claim 8, wherein the first pair of the surface pulse wave measurement unit and the second pair of the PPG measurement unit are disposed adjacently to each other, and wherein the partition is disposed between the first pair of the surface pulse wave measurement unit and the second pair of the PPG measurement unit.

10. The apparatus of claim 7, wherein the surface pulse wave measurement unit is disposed in parallel with the PPG measurement unit.

11. The apparatus of claim 10, wherein the surface pulse wave measurement unit and the PPG measurement unit are disposed to radiate the first light and the second light in a same direction, respectively.

12. The apparatus of claim 7, wherein the biometric signal extractor comprises:

a direct current (DC) component detector configured to extract a DC component of the PPG signal;

a peak detector configured to extract a peak of the surface pulse wave;

a dicrotic notch detector configured to extract a dicrotic notch of the surface pulse wave;

a heart rate detector configured to count a number of surface pulse waves per unit time; and a pulse time detector configured to extract a pulse transit time (PTT) of the surface pulse wave between at least two different positions on the object.

13. The apparatus of claim 12, further comprising an analyzer configured to analyze biometric information including blood vessel elasticity, a flow rate velocity, a degree of arteriosclerosis, a systolic blood pressure, or a diastolic blood pressure of a blood vessel based on the plurality of biometric signal parameters including the DC component, the peak, the dicrotic notch, a heart rate, or the PTT.

14. The apparatus of claim 13, further comprising a display configured to display the extracted plurality of biometric signal parameters.

15. The apparatus of claim 7, wherein the surface pulse wave measurement unit and the PPG measurement unit are disposed in a wearing unit wearable by the object.

16. The apparatus of claim 7, wherein the first light is incoherent light, and the surface pulse wave measurement unit is configured to measure the surface pulse wave of the object based on a change in the intensity of the first light reflected from the surface of the object.

\* \* \* \* \*